US00PP31599P2

(12) United States Plant Patent
Hartman

(10) Patent No.: US PP31,599 P2
(45) Date of Patent: Mar. 24, 2020

(54) ***CALADIUM* PLANT NAMED 'SPLASH OF WINE'**

(50) Latin Name: ***Caladium* X *hortulanum***
Varietal Denomination: Splash Of Wine

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/501,046

(22) Filed: Feb. 13, 2019

(51) Int. Cl.
*A01H 5/02* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 6/10; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Caladium* plant named 'Splash Of Wine', characterized by its short, compact and mounding habit; dense and bushy appearance; vigorous growth habit and rapid growth rate; small fancy-type leaves that have dark green-colored venation with interveinal areas that are white flushed with red and light red in color and densely covered with red purple-colored spots and have narrow dark green-colored margins; and leaf petioles that are light red to light greyed orange and tinged with greyed red in color with dark greenish brown-colored stipples and streaks.

4 Drawing Sheets

Botanical designation: *Caladium* X *hortulanum*.
Cultivar denomination: 'SPLASH OF WINE'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'Splash Of Wine'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2011 in Avon Park, Fla. of *Caladium* X *hortulanum* 'Gingerland', not patented, as the female, or seed, parent with *Caladium* X *hortulanum* 'Candidum', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2012.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2013 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Splash Of Wine'. These characteristics in combination distinguish 'Splash Of Wine' as a new and distinct *Caladium* plant:

1. Relatively short in height and compact and mounding habit; dense and bushy appearance.
2. Vigorous growth habit and rapid growth rate.
3. Relatively small fancy-type leaves that have dark green-colored venation with interveinal areas that are white flushed with red and light red in color and densely covered with red purple-colored spots and have narrow dark green-colored margins.
4. Petioles that are light red to light greyed orange and tinged with greyed red in color with dark greenish brown-colored stipples and streaks.

Plants of the new *Caladium* differ primarily from plants of the female parent, 'Gingerland', in the following characteristics:

1. Plants of the new *Caladium* are shorter than plants of 'Gingerland'.
2. Plants of the new *Caladium* grow faster than plants of 'Gingerland'.
3. Plants of the new *Caladium* and 'Gingerland' differ in leaf color as leaves of plants of the new *Caladium* have dark green-colored venation with interveinal areas that are white flushed with red and light red in color and densely covered with red purple-colored spots and have narrow dark green-colored margins whereas leaves of plants of 'Gingerland' have white-colored interveinal areas, white and pink-colored venation, dark red-colored spots and dark green-colored borders.

Plants of the new *Caladium* differ primarily from plants of the male parent, 'Candidum', in the following characteristics:

1. Plants of the new *Caladium* are shorter than plants of 'Candidum'.
2. Plants of the new *Caladium* and 'Candidum' differ in leaf color as leaves of plants of the new *Caladium* have dark green-colored venation with interveinal areas that are white flushed with red and light red in color and densely covered with red purple-colored spots and have narrow dark green-colored margins whereas leaves of plants of 'Candidum' have distinct green-colored venation with white-colored interveinal areas with development, leaves of 'Candidum' are mostly green in color with white-colored flecks.
3. Plants of the new *Caladium* and 'Candidum' differ in leaf petiole color as leaf petioles of plants of the new *Caladium* are light red to light greyed orange and tinged with greyed red in color with dark greenish brown-colored stipples and streaks whereas leaf petioles of plants of 'Candidum' are green in color with black stripes.

Plants of the new *Caladium* can be compared to plants of *Caladium* X *hortulanum* 'Cranberry Star', disclosed in U.S. Plant Pat. No. 20,792. In side-by-side comparisons, plants of the new *Caladium* differ primarily from plants of 'Cranberry Star' in the following characteristics:

1. Plants of the new *Caladium* are shorter than plants of 'Cranberry Star'.
2. Leaves of plants of the new *Caladium* are rugose and crinkled whereas leaves of plants of 'Cranberry Star' are mostly flat.
3. Plants of the new *Caladium* and 'Cranberry Star' differ in leaf color as leaves of plants of the new *Caladium* have dark green-colored venation with interveinal areas that are white flushed with red and light red in color and densely covered with red purple-colored spots and have narrow dark green-colored margins whereas leaves of plants of 'Cranberry Star' are mostly white in color with green-colored veins and purple-colored spots.

Plants of the new *Caladium* can also be compared to plants of *Caladium* X *hortulanum* 'UF-85-5', disclosed in U.S. Plant Pat. No. 24,681. In side-by-side comparisons, plants of the new *Caladium* differ primarily from plants of 'UF-85-5' in the following characteristics:

1. Plants of the new *Caladium* are shorter than plants of 'UF-85-5'.
2. Leaves of plants of the new *Caladium* are rugose and crinkled whereas leaves of plants of 'UF-85-5' are mostly flat.
3. Plants of the new *Caladium* and 'UF-85-5' differ in leaf color as leaves of plants of the new *Caladium* have dark green-colored venation with interveinal areas that are white flushed with red and light red in color and densely covered with red purple-colored spots and have narrow dark green-colored margins whereas leaves of plants of 'UF-85-5' are white and green in color with red-colored spots.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Splash Of Wine' in a container and grown in a shadehouse (tuber de-eyed).

The photograph at the top of the second sheet is a comparison view of typical plants of 'Splash Of Wine' grown in containers; the plant on the left has not had its tuber de-eyed and the plant on the right has had its tuber de-eyed prior to planting.

The photograph at the bottom of the second sheet is a side perspective view of typical plants of 'Splash Of Wine' grown in an open production field.

The photograph at the top of the third sheet is a comparison view of typical potted plants of the female parent, 'Gingerland' (left), 'Splash Of Wine' (center) and the male parent, 'Candidum' (right).

The photograph at the bottom of the third sheet is a comparison view of typical potted plants of 'Cranberry Star' (left), 'Splash Of Wine' (center) and 'UF-85-5' (right).

The photograph at the top of the fourth sheet is a close-up view of typical freshly-harvested tubers with roots and leaf petioles of 'Splash Of Wine'.

The photograph at the bottom of the fourth sheet is a close-up view of a typical inflorescence of 'Splash Of Wine'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shadehouse were ten weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'Splash Of Wine'.

Parentage:

*Female, or seed, parent.*—*Caladium* X *hortulanum* 'Gingerland', not patented.

*Male, or pollen, parent.*—*Caladium* X *hortulanum* 'Candidum', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments elliptic in shape. Height: About 3.3 cm to 3.9 cm. Diameter: About 6.7 cm to 12 cm. Segment height: About 2.7 cm to 3.2 cm. Segment diameter: About 3.1 cm to 3.4 cm. Axillary bud size: About 4 mm by 4 mm. Texture: Thick, starchy; somewhat brittle. Color: Epidermis, freshly-harvested: Close to 155B variably and faintly tinged with 182D. Epidermis, dried.: Close to 200A. Cortical tissue: Close to 1D and 155C. Axillary buds: Close to 49D. Root description: Thick, fleshy contractile roots with few lateral branches; color, close to N155D. Rooting habit: Medium density to dense.

Plant description:

*Plant type*.—Herbaceous perennial; suitable as a potted plant in containers 15-cm to 25-cm and suitable as a landscape plant in shaded areas.

*Plant and growth habit*.—Relatively short in height and compact and mounded plant habit; inverted triangle and wider than tall; dense and bushy appearance; vigorous growth habit and rapid growth rate; potted plants finish in saleable form in about seven to eight weeks after planting tubers; leaf petioles and leaves arise from one or more growing points on tubers; leaf petioles initially upright and outwardly arching with development.

*Plant height, from soil level to top of foliar plane, shadehouse-grown potted plants*.—About 23 cm to 27 cm.

*Plant height, from soil level to top of inflorescences, shadehouse-grown potted plants*.—About 30 cm.

*Plant diameter or spread, shadehouse-grown potted plants*.—About 30 cm to 36 cm.

*Number of shoots per plant, shadehouse-grown potted plants, tubers not de-eyed*.—About three to four develop per #1 tuber.

*Number of shoots per plant, shadehouse-grown potted plants, tubers de-eyed*.—About four to five develop per #1 tuber.

*Cataphylls, shadehouse-grown potted plants*.—Length: About 6 cm to 8 cm. Width: About 1 cm to 1.6 cm. Shape: Lanceolate. Apex: Acute to acuminate. Base: Sheathing the stem. Color, inner surface: Close to N155C and 155C; colors and patterns on the outer surface are visible on the inner surface. Color, outer surface: Close to 36D and N170D streaked and stippled with close to 200A tinged with 147A; with development, color becoming closer to 199A and 200A.

Leaf description:

*Arrangement and type*.—Alternate; simple; fancy-type.

*Length, shadehouse-grown potted plants*.—About 13 cm to 18 cm.

*Width, shadehouse-grown potted plants*.—About 10 cm to 10.4 cm; when flattened, about 10.7 cm to 11 cm.

*Shape*.—Ovate.

*Apex*.—Acute to acuminate.

*Base*.—Sagittate to peltate.

*Margin*.—Entire; undulate with broad undulations.

*Texture and luster, upper surface*.—Rugose, crinkled, glabrous; dull.

*Texture and luster, lower surface*.—Slightly glaucous; dull sheen.

*Venation pattern*.—Pinnate.

*Color, shadehouse-grown potted plants*.—Developing and fully developed leaves, upper surface: Towards the margins: Close to 139A flecked with close to 145D tinged with 182D and 54C. Leaf edge: Close to N186C. Basal notch: Close to 187A and 60A. Midvein and primary venation: Close to 139A and close to 139A tinged with N189A; at the petiole attachment, close to N186A; areas surrounding venation, close to 53C tinged with 53B. Peripheral venation: Close to 139A and 137A. Interveinal areas: Close to 155A or close to 155A variably flushed with close to 53C and 54C. Random spots: Close to 60A, 60B and 59A. Developing and fully developed leaves, lower surface: Towards the margins: Close to 147A to 147B. Leaf edge: Close to N186C. Basal notch: Close to 187A. Midvein: Close to 147B to 147C. Primary venation: Close to 147A and 147B. Peripheral venation: Close to 144A and 144B. Interveinal areas: Close to 155A or close to 155A variably flushed with close to 185B, 185C, 59C, 59D or 38D. Random spots: Close to 59A and 59B.

*Petioles*.—Aspect: Initially upright and straight and outwardly arching with development; flexible. Length, shadehouse-grown potted plants: About 16 cm to 23 cm. Diameter, distally, shadehouse-grown potted plants: About 3.5 mm to 4 mm. Diameter, proximally, shadehouse-grown potted plants: About 5 mm to 8 mm. Texture and luster: Smooth, glabrous; glaucous and dull; just below leaf junction, slightly glaucous. Color, shadehouse-grown potted plants, when developing and fully developed: Proximally, close to 49D and N170D faintly tinged with close to 182D and stippled and streaked with close to 200A tinged with 147A; distally (just below leaf junction), close to 147C to 147D and 164D variably stippled and streaked with close to 200B. Wing length, shadehouse-grown potted plants: About 3 cm to 4.3 cm. Wing diameter, shadehouse-grown potted plants: About 8 mm. Texture and luster, inner and outer surfaces: Smooth, glabrous; dull to slightly glossy. Wing color, shadehouse-grown potted plants: Inner surface: Close to N155C and 155C; colors and patterns on the outer surface are visible on the inner surface. Outer surface: Close to 182D, N170D and 36D stippled and streaked with close to 147A tinged with 200A.

Inflorescence description: Inflorescences observed on ten week-old shadehouse-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with mint and camphor notes.

*Natural flowering season and flower longevity*.—Plants of the new *Caladium* typically flower during the spring in central Florida; flowers develop about ten weeks after growth commences; inflorescences last about three days before fading; inflorescences persistent.

*Spathe*.—Length, overall: About 9.7 cm. Length, distal open portion: About 6.1 cm. Length, proximal closed portion: About 3.6 cm. Width, distal open portion: About 4 cm. Depth, distal open portion: About 2.2 cm. Width, at constriction: About 1.1 cm. Width, proximal closed portion: About 2 cm. Shape, open portion: Obovate. Apex: Cuspidate. Base: Acute. Margin: Entire; smooth. Texture and luster, front surface: Smooth, glabrous; dull. Texture and luster, rear surface: Smooth, glabrous; dull; proximally, slightly glaucous. Color, front surface: Distal open portion: Close to 155C sparsely speckled and spotted with close to 53A tinged with 187B; with development, color becoming closer to 199B. Proximal closed portion: Close to 147D slightly tinged with close to 187A to 187B; color does not change with development. Color, rear surface: Distal open portion: Close to 155C and 145D; color does not change with development. Proximal closed portion: Close to 147C; color does not change with development.

*Spadix*.—Length, overall: About 6.5 cm. Length, male flower zone: About 3.5 cm. Length, sterile zone: About 1.8 cm. Length, female flower zone: About 1.2 cm. Diameter, male flower zone: About 9 mm. Diameter, sterile flower zone: About 5 mm. Diameter, female flower zone: About 7 mm. Shape: Columnar. Apex: Acute to obtuse. Base: Obtuse. Aspect: Upright. Color, mature, male zone: Close to 155D. Color, mature, sterile zone: Close to 155D. Color, mature, female zone: Close to N155D. Male flowers: Quantity per spadix: About 122. Shape: Obovate. Height: About 3 mm. Diameter: About 3 mm. Pollen amount: Abundant. Pollen color: Close to 11C. Female flowers: Quantity per spadix: About 52. Shape: Obovate. Height: About 1.8 mm. Diameter: About 2.8 mm. Stigma color: Close to N155D. Ovary color: Close to 159C.

*Scape*.—Length: About 20.3 cm. Diameter: About 5.5 mm. Strength: Sturdy; flexible. Aspect: Mostly erect. Texture and luster: Smooth, glabrous; dull; distally, slightly glaucous. Color: Close to 199C tinged with 147C and streaked and stippled with 200A and 200B; distally, close to 147C tinged with close to 145B faintly stippled and streaked with 200D.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'Splash Of Wine' as illustrated and described.

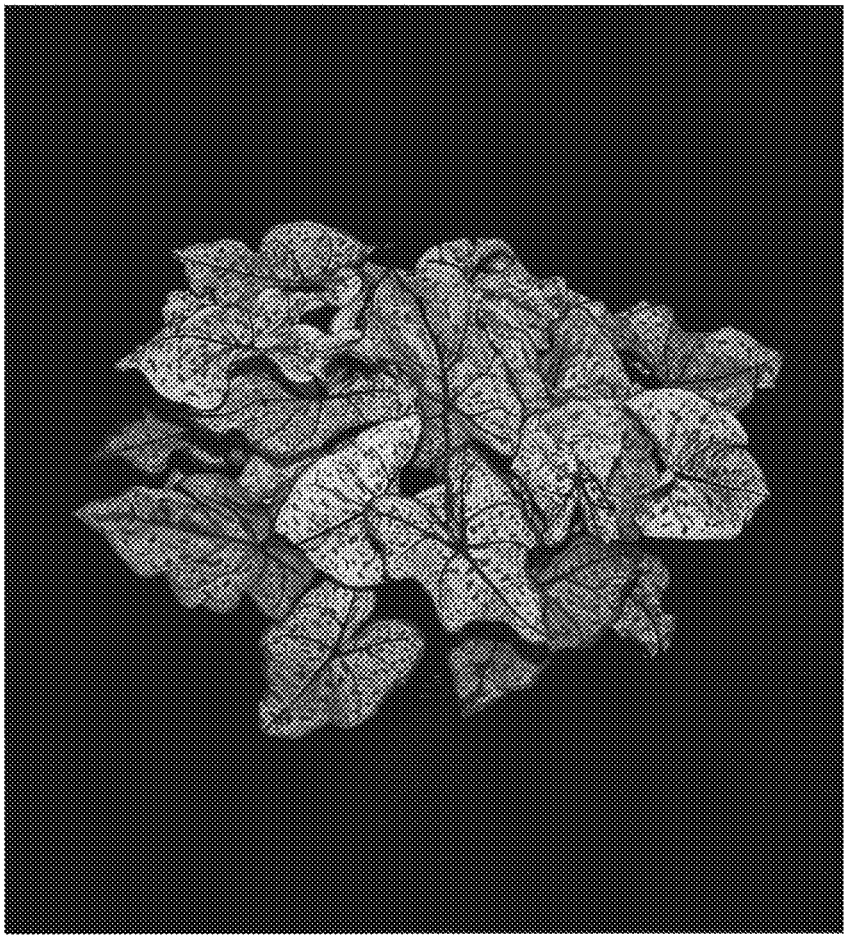

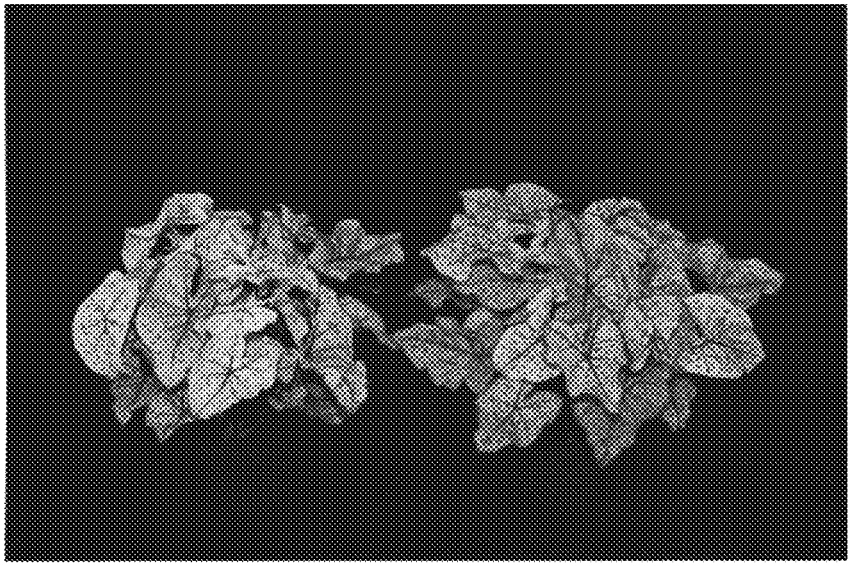
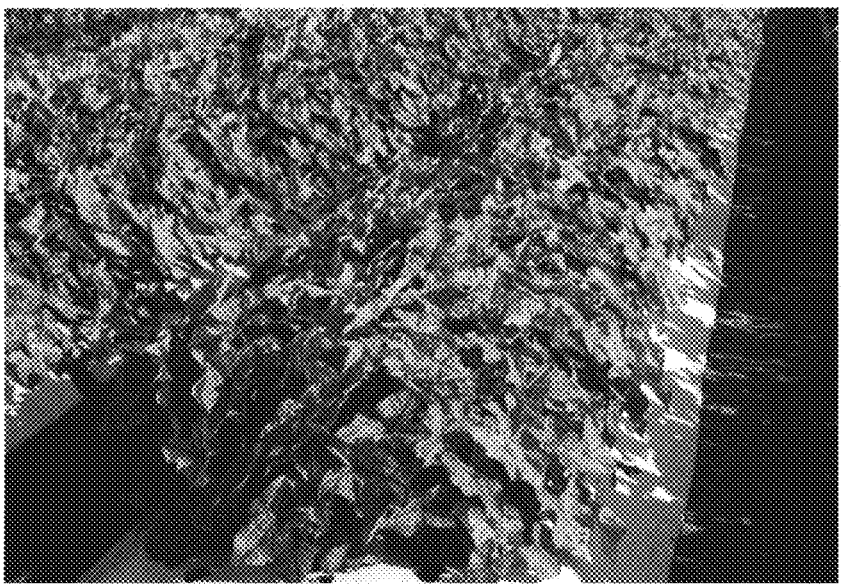

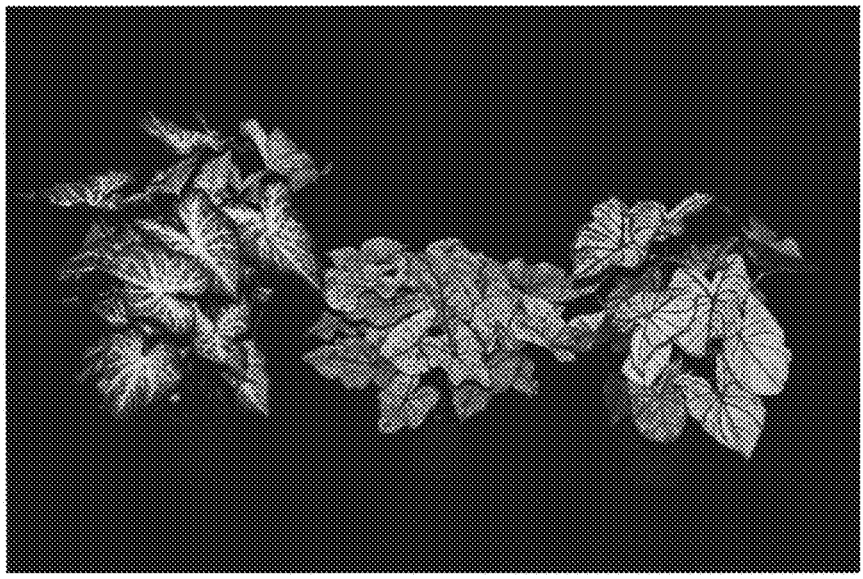
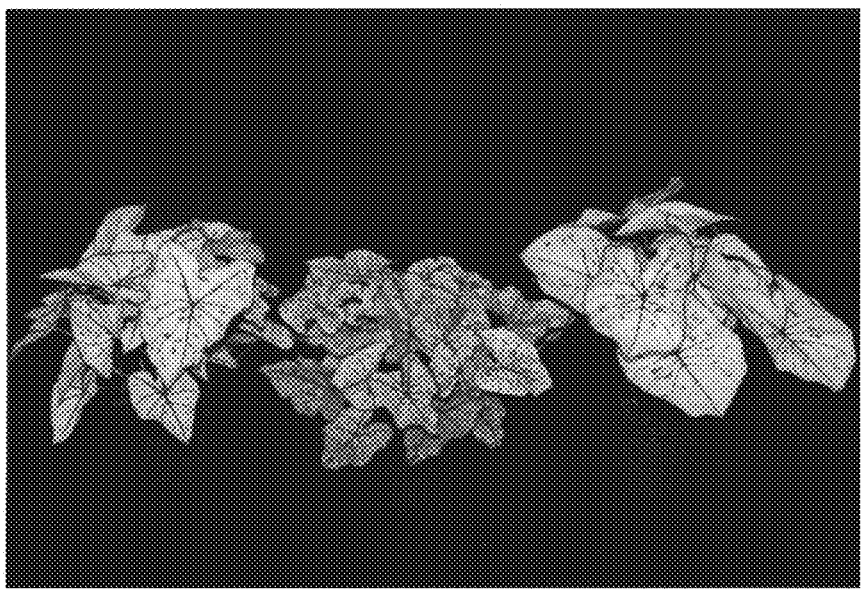

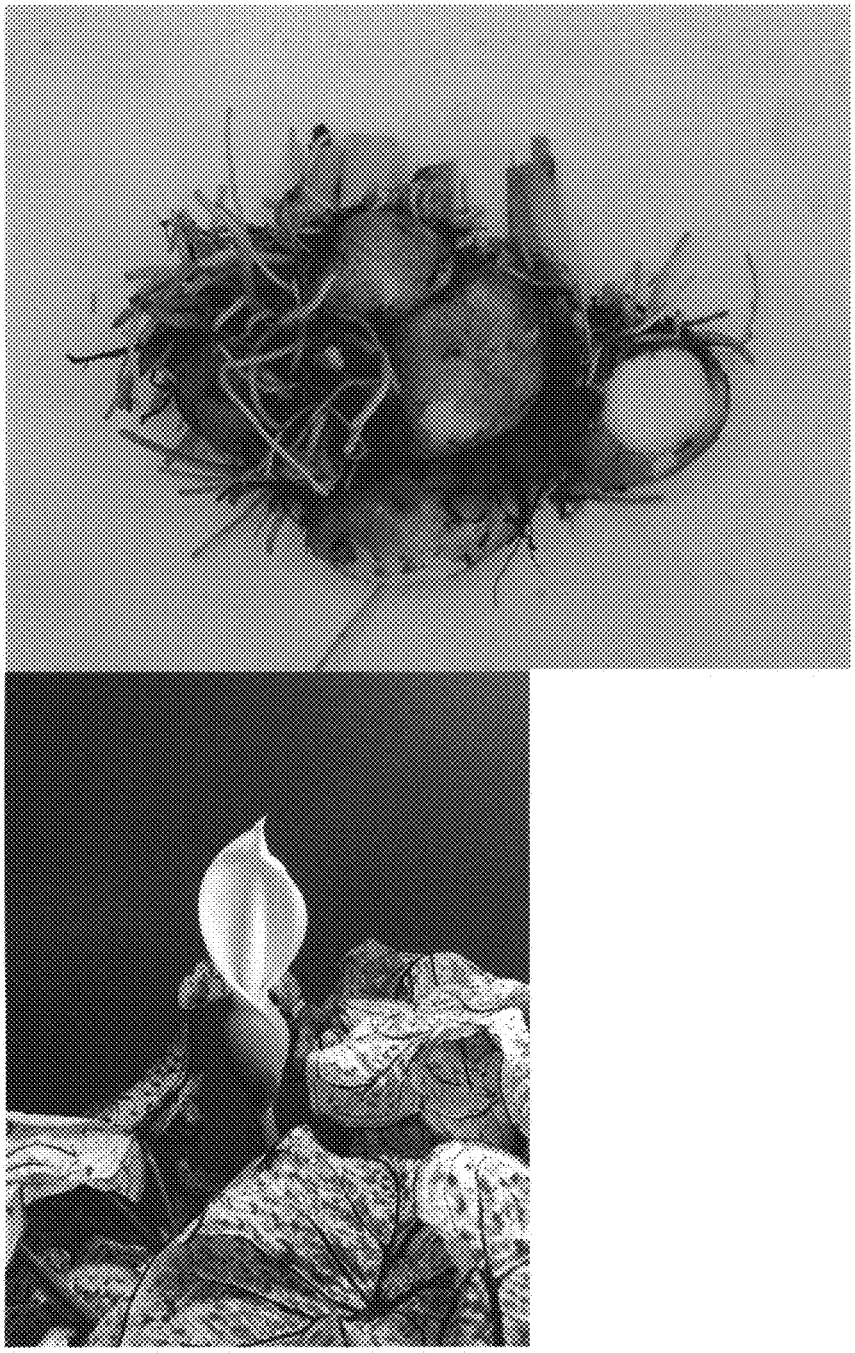

* * * * *